United States Patent
Lefler (12)

(10) Patent No.: US 9,364,526 B2
(45) Date of Patent: Jun. 14, 2016

(54) DIAGNOSTIC, THERAPEUTIC AND A VACCINE AGAINST TREPONEMES

(76) Inventor: Hank (Henry) Michael Lefler, Las Vegas, NV (US)

( * ) Notice: Subject to any disclaimer, the term of this patent is extended or adjusted under 35 U.S.C. 154(b) by 127 days.

(21) Appl. No.: 13/433,258

(22) Filed: Mar. 28, 2012

(65) Prior Publication Data

US 2012/0251578 A1   Oct. 4, 2012

Related U.S. Application Data

(60) Provisional application No. 61/469,041, filed on Mar. 29, 2011.

(51) Int. Cl.
| | | |
|---|---|---|
| *A61K 39/00* | (2006.01) | |
| *A61K 39/02* | (2006.01) | |
| *G01N 33/53* | (2006.01) | |
| *G01N 27/447* | (2006.01) | |
| *G01N 33/571* | (2006.01) | |

(52) U.S. Cl.
CPC .......... *A61K 39/0225* (2013.01); *G01N 33/571* (2013.01); *A61K 2039/522* (2013.01); *A61K 2039/552* (2013.01); *G01N 2333/20* (2013.01)

(58) Field of Classification Search
None
See application file for complete search history.

(56) References Cited

U.S. PATENT DOCUMENTS

| | | |
|---|---|---|
| 4,721,617 A | 1/1988 | Johnson |
| 6,096,323 A | 8/2000 | Walker et al. |
| 6,287,575 B1 | 9/2001 | Walker et al. |
| 6,451,769 B1 | 9/2002 | Huebner et al. |
| 2003/0086947 A1 | 5/2003 | Walker et al. |

OTHER PUBLICATIONS

Riley et al. Applied and Environmental Microbiology, No. 1988, p. 2862-2865.*
The Merck Veterinary Manual. Retrieved on Jan. 27, 2013 from http://www.merckvetmanual.com/mvm/index.jsp?cfile=htm/bc/90530.htm.*
Harlow et al. Antibodies A Laboratory Manual, 1988 Chapter 5, p. 72-74.*
Ellis, R.W. Chapter 29 of "Vaccines" [Plotkin, S.A. et al. (eds) published by W. B. Saunders company (Philadelphia) 1988.*
Abbas et al. Cellular and Molecular Immunology 2000 Chapter 15 p. 360-362.*
Klitgaard et al. "Evidence of Multiple Treponema Phylotypes Involved in Bovine Digital Dermatitis as Shown by 16S rRNA Gene Analysis and Fluorescence in Situ Hybridization" Journal of Clinical Microbiology, vol. 46 No. 9 (2008).

* cited by examiner

*Primary Examiner* — Oluwatosin Ogunbiyi

(57) ABSTRACT

The development of a diagnostic, therapeutic and making and administering a vaccine against ungulate diseases which involves spirochete bacteria in particular, Treponemes.

7 Claims, 2 Drawing Sheets

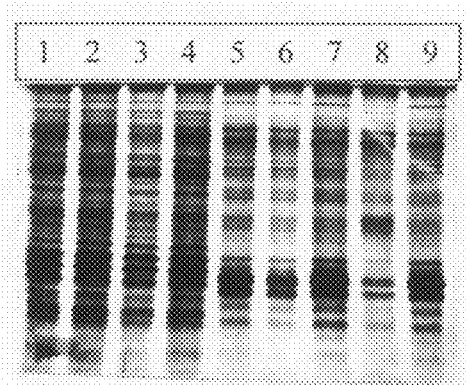
Figure 1. SDS-PAGE (15%)
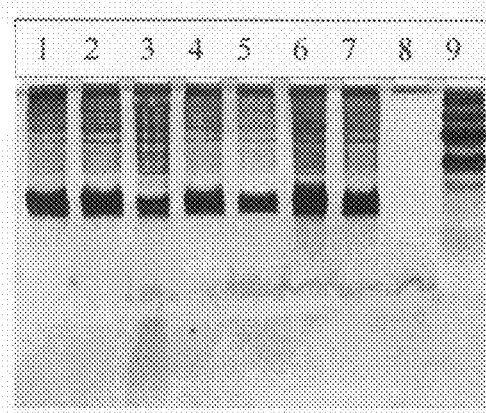
Figure 2. SDS-PAGE (22%)
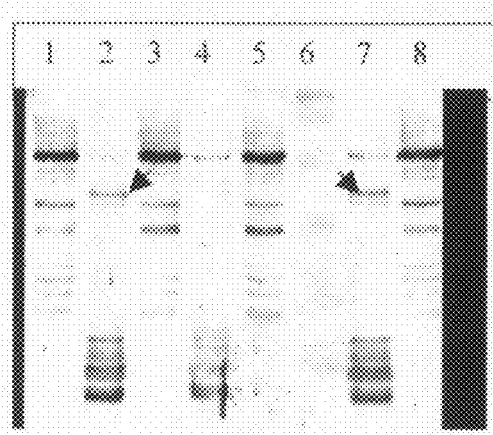
Figure 3. Heterologous Probe.
Lanes 2 and 7 show a 38-49 kDa protein
expressed in 9-3143 cultured in SOT1 with the
addition of HS.

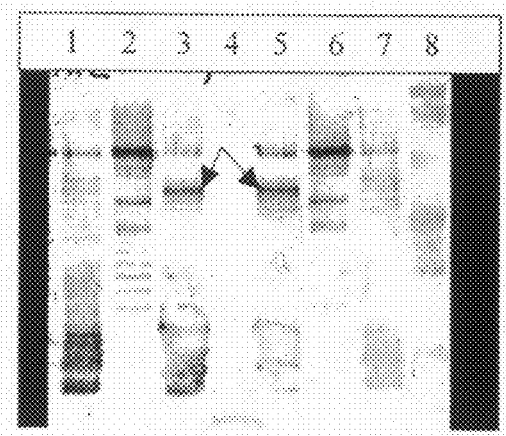
Figure 4. Homologous Probe.
Lanes 3 and 5 show a 38-49 kDa protein expressed in 9-3143 cultured in SOTI with the addition of HS.
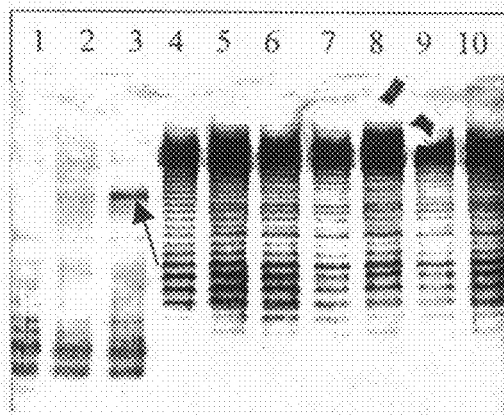
Figure 5. GPT naturally infected cow exhibiting classical DD.
Lane 3 shows a 38-49 kDa protein expressed in 9-3143 cultured in SOTI with the addition of HS.
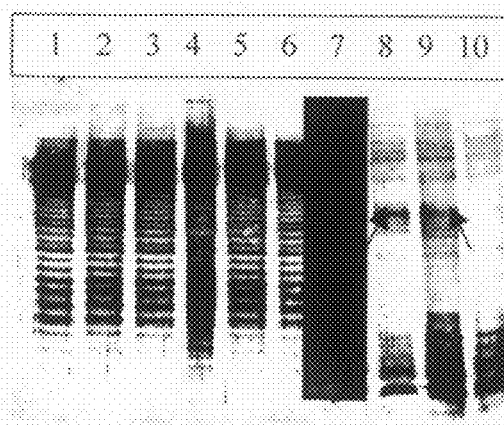
Figure 6. Homologous Probe.
Lanes 8 and 9 show a 38-49 kDa protein expressed in 9-3143 cultured in SOTI with the addition of HS

DIAGNOSTIC, THERAPEUTIC AND A VACCINE AGAINST TREPONEMES

CROSS-REFERENCE TO RELATED APPLICATIONS

This application claims the benefit of priority to U.S. Provisional Patent application No. 61/469,041 filed on 29 Mar. 2011 which is incorporated herein by reference.

FIELD OF THE INVENTION

This invention relates to the prevention of ungulate diseases caused by the spirochete bacteria Treponema; in particular, developing a diagnostic, therapeutic and making and administering a vaccine against the same.

BACKGROUND

There is an increasing incidence of spirochete infections occurring in both the animal and human population. For example, the increase number of cases in syphilis, Treponema pallidum, Lyme disease, Borrelia burgdorferi, and Digital Dermatitis (DD).

While first reported in Italy in 1974, the past 20 years has seen a wide-spread outbreak in a non-viral Papillomatous Digital Dermatitis (PDD) Treponeme infection in cattle throughout Europe and North America; specifically, California. PDD (also referred to as "foot warts" in cattle) has been known to cause severe lameness, body weight loss, and decreased reproductive performance in infected animals. The economic significance is tremendous. The disease situation is spreading rapidly and geographically.

PDD disease is categorized into three stages: Early, intermediate and mature PDD. In early PDD the skin-horn junction of the heel near the inter-digital cleft has a flat red lesion. Intermediated PDD is characterized by a ragged lesion and destruction of the heel horn. The mature PDD has a pronounced raised "hairy wart" appearance with advanced papillae formation.

A Treponeme, Treponema spp, is involved in the pathogenesis of the PDD disease. The disease affects every aspect of the dairy and beef industry from milk production to reproductive performance and is extremely contagious with some cases affecting 90% of a given herd. In addition to bovine PDD another ungulate, the ovine, has shown ulcerative lesions, primarily around the coronary band, which also results in severe lameness. Although the exact causative agent has not yet been identified in Contagious Ovine Digital Dermatitis (CODD), the PDD related Treponema spp has been isolated and characterized. Currently, it is not known whether or not PDD, and/or CODD can spread to additional species, such as, having an affinity for humans.

Since the effectiveness of the present methods of treatment are limited, a need exists for a specific diagnostic, a functional therapeutic and a vaccine, such as a non-whole-cell vaccine, which is effective to immunize high-risk individuals and susceptible domestic animals against Treponemes, PDD and CODD.

SUMMARY

Even though Syphilis has been around for centuries, a reliable, reproducible in vitro media to cultivate Treponema pallidum has been unsuccessful. Another Treponeme, Treponema denticola, the organism implicated in gingivitis, is associated with sixty phylotypes of oral spirochetes present in the tissue; however cultivating the spirochetes in an in vitro media has been unsuccessful. Kiltgaard et al. "Evidence of Multiple Treponema Phylotypes Involved in Bovine Digital Dermatitis as Shown by 16S rRNA Gene Analysis and Fluorescence In Situ Hybridization" Journal of Clinical Microbiology, Vol. 46 No. 9 (2008), For example, another spirochete, Borrelia burgdorferi, which is believed to be the causative agent for Lyme disease, can remain in human tissue for years after infection. However, it has been found that if Borrelia is removed, isolated and passaged and/or subcultured in an artificial in vitro culture medium like Barbour-Stoenner-Kelly (BSK) and Barbour-Stoenner-Kelly-Harvard (BSK-H,) commercially available from Sigma, for as little as 25 passages, Borrelia loses its ability for infection and pathogenesis. Additional passages of Borrelia produced Outer Surface Protein (OSP)-less mutants and these mutants are no longer resistant to our innate defense. Sadziene et al. "Antibody Mutants of Borrelia burgdorferi: In Vitro Selection and Characterization" J Exp Med, 176: 799-809 (1992)

It is believed that the OSP-less mutants are the most in vitro adapted non-pathogenic strain of Borrelia, which may result in the furthest removed pathogenic strain of Borrelia based on the artificial in vitro "diet."

It has been well documented for isolation of the spirochetes involved in PDD/CODD that biopsies from Digital Dermatitis (DD) infected animals are taken from hoof skin via biopsies and placed in an in vitro media, an artificial environment. (Walker et al., Vet. Micro. 47:343-355 (1995). In Walker et al. and as a general standard in the art, once the spirochetes are isolated, the very same natural food source, the biopsy (e.g., the infected hoof skin that is used for isolation) is effectively removed and is no longer present in subsequent media culture passaging and/or in subsequent subculturing of the Treponemes in media. The spirochetes are forced to adapt in their new microenvironment or perish. Any time any microorganism is removed from its natural environment, the microorganisms are forced to adapt or perish. Subsequently, it is believed that the microorganisms that have best adapted to the artificial environment are the microorganisms that are subcultured and/or passaged from one in vitro culture to the next. Eventually, the organisms that are selected are those most suited to their new microenvironment and furthest removed from their natural environment.

In accordance with some embodiments of the present invention, the spirochetes are cultivated and/or grown and/or passaged and/or subcultured and/or co-cultured and/or co-cultivated, separate and distinct from isolated and/or identified as a pure culture of Treponemes, in a media that is most representative of its natural environment of pathogenesis. That is, the spirochetes are fed the same or substantially the same "food" off of which the spirochetes have been living on, such as the hoof, hoof hair and hoof skin, skin of ungulates, human hair, skin and gingival tissue. In this regard, embodiments of the present invention adds compounds and/or is grown, passaged, subcultured and/or is co-cultured and/or is co-cultivated in media that is part of the pathogenesis of DD, referred to herein as HS.

Moreover, it is believed that when Treponemes are grown in an in vitro media culture without HS, the Treponemes are not upregulating selective genes and expressing selective proteins. In addition, if the Treponemes are grown in an in vitro media culture minus the HS and used as the immunizing agent, it is believed that there would not be any antibodies to a protein that is not there. Therefore, PDD infected cows, and/or DD infected animals, should have an immune response (production of antibodies) to the protein(s) if this up-regulation and protein(s) expression (induced by culture media with HS) is representative of what happens in a real life infection.

We have be able to demonstrate that sera from all of the naturally infected PDD cows tested thus far showed specific immunoblot reactivity to the protein induced in the Treponemes with the addition of HS. It is believed that this has never been seen or reported before.

Some embodiments of the present invention are directed to a diagnostic, therapeutic and/or a vaccine that is effective to immunize animals against PDD and DD. The diagnostic can help to determine Treponemal infection and/or exposure. The therapeutic can help the animal or individual reduce or eliminate the infection. The non-whole-cell vaccine comprises of an effective amount of either inactivated *Treponema* spirochete fragments or polypetides therefrom that can be derived from infected hosts and cultured, and/or grown and/or co-cultured and/or co-cultivated in subcultures or passages in a suitable medium including HS and derivatives of HS. This is separate and distinct from isolated and/or identified as a pure Treponeme and/or pure *Treponema* culture. The non-whole-cell immunogenic spirochetes or subunits thereof are suspended in a physiologically-acceptable, non-toxic liquid vehicle to yield an injectable vaccine.

BRIEF DESCRIPTION OF THE DRAWINGS

Embodiments of the invention will be described by way of example only, with reference to the drawings, in which FIG. 1 is an example of a silver stained 15% Sodium Dodecyl Sulfate-Polyacrylamide Gel Electrophoresis (SDS-PAGE) of Treponemes involved in DD.

FIG. 2 is an example of a silver stained 22% SDS-PAGE of Treponemes involved in DD.

FIG. 3 is an example of an immunoblot which shows the 38-49 kDa protein expression, specifically lanes 2 and 7, when DD isolate Type I (9-3143) is cultured in a medium containing HS and probed with naturally DD infected Type II bovine serum heterologous to Type I.

FIG. 4 is an example of an immunoblot which shows the 38-49 kDa protein expression, specifically lanes 3 and 5, when DD isolate Type I (9-3143) is cultured in a medium containing HS and probed with naturally DD infected bovine serum homologous to Type II.

FIG. 5 is an example of an immunoblot which shows the 38-49 kDa protein expression, specifically lane 3, when DD isolate Type I (9-3143) is cultured in a medium containing HS and probed with naturally DD infected bovine serum.

FIG. 6 is an example of an immunoblot which shows the 38-49 kDa protein expression, specifically lanes 8 and 9, when DD isolate Type I (9-3143) is cultured in a medium containing HS and probed with naturally DD infected Type I bovine serum, homologous to Type I, from which Type I (9-3143) was isolated.

DETAILED DESCRIPTION OF THE PREFERRED EMBODIMENT

In the following description of preferred embodiments, reference is made to the accompanying drawings which form a part hereof, and in which it is shown by way of illustration specific embodiments in which the invention may be practiced. It is to be understood that other embodiments may be utilized and changes may be made without departing from the scope of the preferred embodiments of the present invention.

The following examples are provided by way of illustration only and not by way of limitation. Those of skill in the art can readily recognize a variety of non-critical parameters that could be changed or modified to yield essentially similar results.

Origin and Cultivation of *Treponema*.

Treponemes have been implicated as one of the causative agents of PDD. As described in Walker et al., "Spirochetes isolated from dairy cattle with papillomatous digital dermatitis and interdigital dermatitis" Veterinary Microbiology 47: 343-355 (1995), and is standard in the art, after the initial isolation of the Treponemes using the original biopsy or tissue sample, any subcultures and/or passages of the Treponemes are performed in media or culture media absent of the original biopsy or tissue sample. Additional subcultures and/or passages, again absent of any biopsy or tissue samples in the subculture media or culture media and/or passage media, are performed to determine type and/or group, strain and/or isolate and a pure culture of the same. Initially, the PDD spirochetes were classified into two groups. Type I consisting of isolates 1-9185 MED (American Type Culture Collection (ATCC) Accession No. 202030), 9-3528, 9-3143 and Type II consisting of isolates 2-1498 (ATCC Accession No. 202031), 7-2009 and 9-3301. DNA sequencing of the above spirochetes and additional spirochetes are discussed in U.S. Pat. Nos. 6,287,575, 6,096,323 and U.S. patent application Ser. No. 09/516,043, the entire contents of each of which is hereby incorporated by reference in its entirety.

The following illustrative examples use four strains of PDD: Type I, isolate 9-3143 and Type II, isolates 2-1498, 9-3301 and 7-2009. As previously reported in, for example, U.S. Pat. Nos. 6,287,575, 6,096,323 and U.S. patent application Ser. No. 09/516,043, which are hereby incorporated by reference in their entireties, PDD *Treponema* spps Type I isolate 9-3143 has a high—greater than 98%—DNA homology to *Treponema denticola*; whereby Type II, isolates 2-1498, 9-3301 and 7-2009, are more closely related to the human skin pathogen, *Treponema phagedenis*.

Preparation, culture conditions and storage of bacterial isolates for culture.

In the following examples, all bacterial cultures were aliquoted into 1.5 ml Nalgene, cyro-freezer vials with 15% glycerol or MicroBank (commercially available from PRO-LAB Diagnostics, Austin, Tex.) and stored at −70° C. or in liquid nitrogen tanks.

Media for cultivation and growth varies, such as but not limited to, Oral Treponeme Isolation broth, enrichment (OTI, OTI-E), commercially available from Anaerobe Systems, Morgan Hill, Calif. BSK, BSK-H, (Sigma) Peptone-yeast Trepomene broth (Difco), PDDTp, Yano, T., R. Yamagami, K. Misumi, C. Kubota, K. K. Moe, T. Hayashi, K. Yoshitani, O. Ohtake, and N. Misawa, "Genetic heterogeneity among strains of *Treponema phagedenis*-like spirochetes isolated from dairy cattle with papillomatous digital dermatitis in Japan." J. Clin. Microbiol. 47:727-733, (2009), OMIZ-Pat, C. Wyss, B. K. Choi, P. Schupbach, B. Guggenheim and U. B. Gobel "*Treponema maltophilum* sp. nov., a Small Oral Spirochete Isolated from Human Periodontal Lesions" Int J Syst Bacteriol 46, 745-752 (1996); and/or ATCC medium 2131, 1828 and the like, (ATCC, Manassas, Va.) OTI and Simplified OTI (SOTI) supplemented with a variety of sera and/or individual serum such as rabbit, horse, sheep, goat and cow, at various concentrations, under anaerobic and/or microaerophilic conditions and in the presence or absence of carbon dioxide.

In an example, all four isolates were maintained in glass screw capped tubes consisting of 6.0 ml of Oral Treponeme Isolation broth, enrichment (OTI-E), Anaerobe Systems. Routine passages of the isolates were performed in OTI-E, OTI or a Simplified Oral Treponeme Isolation media (SOTI) with 0.5-1.0 ml of source inoculum and incubated at 33° C. After 2-9 days of incubation, the cultures were either, frozen, sub-cultured, passaged or harvested.

Harvested cultures were centrifuged, washed two times in PBSS, reconstituted with double distilled water and stored at −20° C. As an example, SOTI and Fatty Acid Mix were made as follows:

Preparation of Fatty Acid Mix 300 ml of Fatty Acid Mix, pH 6.0, was prepared with the following ingredients:

| | |
|---|---|
| Sigma Acetic acid (glacial) | 1.7 ml |
| Sigma Propionic acid | 0.6 ml |
| Sigma N-butyric acid | 0.4 ml |
| Sigma N-valeric acid | 0.1 ml |
| Sigma Isovaleric acid | 0.1 ml |
| Sigma Isobutyric acid | 0.1 ml |
| Sigma Alpha-methyl butyric acid | 0.1 ml |
| Added $H_2O$ to | 300 ml |
| Neutralized to pH of 6.0 with 30% NaOH | |

Preparation of SOTI Medium 90 ml medium, pH 6.53, was prepared with the following ingredients:

| | |
|---|---|
| Difco Proteose peptone #2 | 1.0 g |
| Sigma Yeast extract | 1.0 g |
| Sigma $K_2HPO_4$—$3H_2O$ | 0.26 g |
| Sigma NaCl | 0.5 g |
| Sigma Soluble starch | 0.1 g |
| Sigma Glucose | 0.1 g |
| Fatty Acid Mix | 3 ml |
| Distilled Water | 87 ml |

The ingredients were boiled in water bath for 15 minutes. Then 0.06 g Cysteine-HCl was added, and the mixture was autoclaved for 15 minutes. The mixture was then cooled to 50° C. and 10 ml of inactivated sterile calf serum was added.

Protein Evaluation

In this example, all Treponeme isolates were grown under standard anaerobic or reduced oxygen, with or without carbon dioxide conditions. Previously washed or washed and frozen bacteria were assayed for protein under standard procedures as generally described for example in Bradford, M., "A Rapid and Sensitive Method for the Quantitation of Microgram Quantities of Protein Utilizing the Principle of Protein-Dye Binding" Anal. Biochem. 72:248-254 (1976), "Sigma Modified Lowry Protein Assay," Sigma Procedure No. P 5656, "Bio-Rad Protein Assay," Bio-Rad catalog p. 60 (1991), Cabib, E. and Polacheck, I., "Protein assay for dilute solutions." Methods in Enzymology, 104:318-328, (1984).

The following is an example of protein evaluation: protein evaluation was performed using Bio-Rad protein assay in 96 well PVC plates and with a MicroElisa Autoreader, MR580. Samples were run in duplicate and were plotted for linear regression and ANOVA statistics as generally described and is well known in the art.

Homologous and Heterologous Bovine Sera Used were as Follows:

9-3143 serum obtained from the cow which the PDD Type I, 9-3143 was isolated is homologous for Type I and heterologous for Type II. 9-3301 serum obtained from the cow which the PDD Type II, 9-3301 was isolated is homologous for Type II; heterologous for Type I. GPT serum obtained from a cow that exhibited classical PDD and negative cow serum (data not shown), as described in U.S. Pat. Nos. 6,287, 575, 6,096,323 and U.S. patent application Ser. No. 09/516, 043, the contents of each of which is hereby incorporated by reference in its entirety.

Sodium Dodecyl Sulfate-Polyacrylamide Gel Electrophoresis (SDS-PAGE) stacking and resolving gel concentrations varies and may be coupled with the desired volts, amperes and duration of resolution as is generally described in Laemmli, U. K. Nature 227, 680-689 (1970), Chrambach, A., Jovin, T. M., Electrophoresis, 4. 190-204, (1984).

For example, FIG. 1 and FIG. 2 illustrates a 15% and 22% silver stained SDS-PAGE resolving gel, respectively, at 120 constant volts for 100 minutes using a side by side mini-gels, Bio-Rad Mini protean 3 Cell, Power pac 200. Silver stains were performed by standard procedures with varying modifications for proteins, glycoproteins and lipids in accordance with procedures generally described in Switzer R. C. 3rd, Merril C. R., Shifrin S. "A highly sensitive silver stain for detecting proteins and peptides in polyacrylamide gels." Anal Biochem. 98 (1): 231-237 (1979), Morrisey J. H., "Silver stains for proteins in polyacrylamide gels; a modified procedure with enhanced uniformed sensitivity," Anal. Biochem 117, 307-310, (1981), Fomsgaard et al. "Modification of the Silver staining technique to detect lipopolysaccharide in polyacrylamide gels," J. of Clinical Microbiology, 28 No. 12, 2627-2631, (1990).

For example, in FIG. 1 and FIG. 2, each protein assayed bacterial sample was mixed with sample buffer containing SDS (4%), 2-mercaptoethanol (0.4%), bromophenol blue (0.2%), glycerol (35%), and Tris base (0.38%) at pH 6.8 and heated in a water bath at 98° C. for 15 min. Eight microliters was used and the gel was visualized by silver stain.

In FIG. 1, lane 1 is 7-2009 cultivated in OTI, lane 2 is 7-2009 cultivated in SOTI, lane 3 is 7-2009 cultivated in OTI, lane 4 is 7-2009 cultivated in SOTI, lane 5 is 9-3143 cultivated in SOTI, lane 6 is 9-3143 cultivated in SOTI, lane 7 is 9-3143 cultivated in SOTI, lane 8 is 9-3143 cultivated in SOTI and lane 9 is 9-3143 cultivated in OTI.

In FIG. 2, lane 1 is 7-2009 cultivated in OTI, lane 2 is 7-2009 cultivated in SOTI, lane 3 is 7-2009 cultivated in OTI, lane 4 is 7-2009 cultivated in SOTI, lane 5 is 9-3143 cultivated in SOTI, lane 6 is 9-3143 cultivated in SOTI, lane 7 is 9-3143 cultivated in SOTI, lane 8 is empty and lane 9 has the Molecular Weight Markers (MWM) range, starting from the top, of 97.4-104, 66.2-82, 45-48.3, 31-33.4, 21.5-28.3, 14.4-19.4 kDa.

Immunoblots vary and may be coupled with the desired buffers, volts, amperes and duration of transfer, type and pore size of nitrocellulose and/or appropriate matrix as is generally described in Gershoni, J. M., et al. "Protein blotting in uniform or gradient electric fields." Anal. Biochem., 32-40, 144 (1985), Gershoni, J. M., Palade, G. E., "Protein blotting: Principles and applications." Anal. Biochem., 1-15, 131 (1983), Gershoni, J. M., Palade, G. E., "Electrophoretic transfer of Proteins from sodium dodecyl sulfate-polyacrylamide gels to a positively charged membrane filter." Anal. Biochem., 396-405, 124 (1982).

For example, FIG. 3 illustrates a 15% SDS-PAGE resolved protein gel transferred to 0.45 micron nitrocellulose paper (Hoeffner and/or Bio Rad, Richmond, Calif.) by using a Bio Rad Mini Trans-Blot Electrophoretic Transfer Cell at 100 constant volts for 60 minutes using a Bio Rad Power pac 200 and standard transfer buffers.

The immunogenic whole-cell isolate treated with HS which is employed as the active component of the present diagnostic, therapeutic and/or vaccines consists essentially of HS activated *Treponema* spirochetes. The HS activated spirochetes are separate and distinct from isolated Treponemes and identical to the embodiment of Treponemes subcultured, and/or grown and/or co-cultured and/or co-cultivated and/or passaged in media or culture media containing HS. The spirochetes can then be separated from the medium by centrifugation, filtration, selective media and culture conditions and the like.

Treponeme proteins expression with the addition of treated or non-treated HS to media, and/or subcultured, and/or grown and/or co-cultured and/or co-cultivated and/or passaged in media or culture media containing treated or non-treated HS can be employed to fish out the corresponding encoding gene for the Treponeme. The encoded gene or genes and/or target gene or genes can be introduced and expressed in a suitable bacterial or vector host and employed as a subunit vaccine, diagnostic or therapeutic. Techniques used currently known in the art and discussed in U.S. Pat. Nos. 6,287,575, 6,096, 323 and U.S. patent application Ser. No. 09/516,043.

The non-whole-cellular isolate can be dried by lyophilization or frozen of an aqueous suspension thereof to yield deactivated non-whole-cells or the encoding gene or genes can be ligated to a plasmid and/or, electroplated and incorporated into a proper cellular host and/or recombined with an appropriate vector such as Recombinant Subunit and/or Recombinant Vectored vaccines.

The treated and/or dried non-whole-cells, subunit or recombined DNA and/or "genetic sequence" may then be adjusted to an appropriate concentration, optionally combined with a suitable vaccine adjuvant, and packaged for use. Suitable adjuvants include but are not limited to: surfactants, e.g., hexadecylamine, octadecylamine, lysolectithin, dimethyl-dioctadecylammonium bromide, N,N-dioctadecyl-N'-N-bis(2-hydroxyethyl-propane diamine), methoxyhexadecylglycerol, and pluronic polyols; polyanions, e.g., pyran, dextran sulfate, dipeptide, dimethylglycine, tuftsin; oil emulsions; and alum. In addition, the immunogenic product may be incorporated into liposomes for use in a vaccine formulation, or may be conjugated to polysaccharides or other polymers.

The absolute weight, quantity and specificity can depend upon factors such as the age, weight and physical condition of the subject considered for diagnostic, therapeutic and/or vaccination. Such factors can be readily determined by the clinician or veterinarian employing animal models or other test systems which are all known to the art. A unit dose of the vaccine or therapeutic can be administered parenterally, e.g., by subcutaneous or by intramuscular injection.

Furthermore, it is expected that the sensitivity and/or specificity of a diagnostic, and/or efficacy of therapeutics and/or vaccines based on *Treponema* spirochetes can be increased by employing purification and/or sequencing of immunogenic fractions derived therefrom by methods which are known to the art. For example, the Treponemal outer envelope which surrounds the protoplasmic cylinder of spirochetes can be readily extracted Klaviter E. C. et al., Acta. Trop., 36, 123 (1979). This fraction may provide immunogens that impart an equal or greater resistance to PDD/CODD infection when employed as the active component of vaccines prepared in accord with the present invention. Recombinant proteins or vector expression may also be used as an immunogens, diagnostics and therapeutics.

Embodiments of the present invention will be further described by reference to the following detailed examples.

The addition of HS and/or grown and/or co-cultured and/or co-cultivated and/or passaged and/or subcultured with HS was derived based on the location of the Treponemes pathogenesis. The evidence for adding HS or co-culturing with HS, separate and distinct from the original biopsy material, was based on the following. Skin and/or hoof skin, in the form of a biopsy, is used for the very isolation of the spirochetes. Skin and/or hoof skin is where, why and how the Treponemes live and cause infection. Moreover, the incidence of PDD occurs primarily during the wet season. Read and Walker published on the experiment transmission PDD by compromising the epidermal barrier, continuous wetting of the feet similar to the natural environment for cattle during the wet season and relative anaerobiosis of the feet as discussed in U.S. Pat. No. 6,287,575.

We theorized there must be a common denominator between the water and the anaerobic conditions. We concluded cellular change likely occurs and this cellular change allows for the Treponemes to cause infection. We know from experience that if we stay too long in the bathtub our skin "prunes." The smooth configuration of the skin is altered. In one example, the difficulty of experimentally controlling the "human and/or animal" hair and skin alteration was achieved by adding either 2-Mercaptoacetic acid or Thioglycolic acid as an example of a treated HS. It is believed 2-Mercaptoacetic acid breaks the disulfide bonds altering the HS. This treatment of HS is similar to the use of 2-Mercaptoacetic acid in hair perms.

The HS was mechanically harvested and collected, in this example, human hair and skin, into small uniform pieces. The small uniform pieces of HS were derived using an electric and/or electro-shaver and shaving twice a day. A similar procedure can be employed in ungulate skin. In the need to add or treat anchor-dependent primary cell cultures or Continuous Cell Lines (CCL), methods can be employed such as a sterile "rubber policeman," sterile scrapper and/or trypsin-versene (Trypsin-EDTA) like compounds, as generally described and is known in the art.

In one example, 50 milligrams of HS were autoclaved for 5 min with 1 ml. 0.8% 2-mercaptoacetic acid (pH 3.65) in 25 ml glass screw cap tubes. 18 mls of freshly prepared SOTI (as described above but with and without Cysteine-HCl) with a final pH of 6.76, autoclaved for 15 minutes, allowed to cool and 10% inactivated sterile calf serum was added to the tubes. The tubes were inoculated with 1.0 ml of OTI-E stationary cultures (2-9 days old) with Type I, isolate 9-3143 and Type II isolates 2-1498 and 7-2009. The PDD Treponeme isolate, either or both 2-1498 or 7-2009 served as the control. In addition, either contemporaneously or previously cultivated, centrifuged, washed or frozen Type I, isolate 9-3143 grown in OTI-E, OTI or SOTI without HS served as an additional control.

In this example, the Treponeme cultures were incubated for 5-9 days at 33° C., centrifuged, washed two times in distilled water. The washed, centrifuged samples were either frozen at ⁻20° C. or used for protein assay, SDS-PAGE, and/or immunoblots. See FIG. 4 and FIG. 5.

The results repeatedly demonstrated an immunological significant protein expression at the 38-49 kDa range as shown above. The arrow indicates the HS induce protein elucidated when probed with sera from naturally PDD infected cows. See FIG. 3, FIG. 4, FIG. 5 and FIG. 6.

In FIG. 3, FIG. 4, FIG. 5 and FIG. 6 either homologous or heterologous naturally DD infected bovine serum served as the primary antibody. A 15% SDS-PAGE resolving gel was transblotted to a 0.45 micron nitrocellulose paper at 100 volts for 60 minutes, blocked with 5% evaporative milk in PBS, washed 3×PBS/Tween and incubated with goat anti-bovine IgG labeled with alkaline phosphate (KPL). Detection was performed with (BCIP/NBT) substrate system (Bio Rad/Sigma).

FIG. 5 and FIG. 6 is an example of a 15% SDS-PAGE gel resolved for a shorter duration prior to the transblott.

FIG. 3 is an example of an immunoblot with a heterologous probe. Type II, 9-3301 naturally DD infected bovine serum is heterologous to Type I and homologous to Type II served as the primary antibody diluted at 1:500. Lanes 2 and 7 show a 38-49 kDa protein expressed in 9-3143 cultivated in SOTI with the addition of HS. Lane 1 is 2-1498 cultivated in SOTI with the addition of HS, Lane 3 is 2-1498 cultivated in OTI with the addition of HS, lane 4 is 9-3143 cultivated in SOTI, lane 5 is 2-1498 cultivated in SOTI, lane 6 has the Molecular Weight Markers (MWM) range, starting from the top, of 97.4-104, 66.2-82, 45-48.3, 31-33.4, 21.5-28.3, 14.4-19.4 kDa and lane 8 is 2-1498 cultivated in OTI.

FIG. 4 is an example of an immunoblot with a homologous probe. Type II, 9-3301 naturally DD infected bovine serum is homologous to Type II and heterologous to Type I served as the primary antibody diluted at 1:500. Lanes 3 and 5 show a 38-49 kDa protein expressed in 9-3143 cultivated in SOTI with the addition of HS. Lane 1 is 9-3143 cultivated in OTI-E, lane 2 is 2-1498 cultivated in OTI with the addition of HS, lane 4 is empty, lane 6 is 2-1498 cultivated in SOTI with the addition of HS, lane 7 is 9-3143 cultivated in OTI, lane 8 has the Molecular Weight Markers (MWM) range, starting from the top, of 97.4-104, 66.2-82, 45-48.3, 31-33.4, 21.5-28.3, 14.4-19.4 kDa.

FIG. 5 is an example of an immunoblot. Serum from a naturally DD infected cow exhibiting classical PDD served as the primary antibody diluted at 1:400. Lane 3 shows a 38-49 kDa protein expressed in 9-3143 cultivated in SOTI with the addition of HS. Lane 1 is 9-3143 cultivated in OTI, lane 2 is 9-3143 cultivated in OTI-E, lane 4 is 2-1498 cultivated in OTI, lane 5 is 2-1498 cultivated in OTI-E, lane 6 is 2-1498 cultivated in SOTI with the addition of HS, lane 7 is 2-1498 cultivated in SOTI with the addition of HS, lane 8 is 2-1498 cultivated in SOTI, lane 9 is 2-1498 cultivated in OTI-E, lane 10 is 2-1498 cultivated in OTI.

FIG. 6 is an example of an immunoblot with a homologous probe. Type I, 9-3143 naturally DD infected bovine serum is homologous to Type I and heterologous to Type II served as the primary antibody diluted at 1:500. Lanes 8 and 9 show a 38-49 kDa protein expressed in 9-3143 cultivated in SOTI with the addition of HS. Lane 1 is 2-1498 cultivated in SOTI with the addition of HS, Lane 2 is 2-1498 cultivated in SOTI with the addition of 2-mercaptoacetic acid, lane 3 is 2-1498 cultivated in SOTI, lane 4 is 2-1498 cultivated in SOTI, lane 5 is 2-1498 cultivated in SOTI, lane 6 is 2-1498 cultivated in SOTI, lane 7 is BLOCKED, lane 10 is 9-3143 cultivated in OTI-E.

It is believed that any Treponeme that has a greater than 98% DNA homology to *T. denticola*, as measured by, including but not limited to, 16s ribosomal DNA and/or 16S rRNA, and/or to *T. denticola* itself, can exhibit the up-regulation of a gene or genes and/or subsequent protein expression at the 38-49 kDa range when grown and/or cultivated in HS. In addition and it is believed, any Treponeme when fed homologous or heterologous HS or derivatives of HS can induce a gene or genes that results in protein expression as an embodiment of the instant invention. The homologous or heterologous HS or derivatives of HS includes but are not limited to skin and/or ungulate skin, human hair and skin, gingival tissue, skin explants, synthesized skin, primary cell cultures, primary cell cultures of keratinocytes, and/or epidermal cells, secondary or continuos cell cultures of keratinocytes, and/or epidermal cells, Continuous Cell Cultures Lines or Continuous Cell Lines (CCL) either anchor-dependent such as Bovine Turbinates (BT), Madin-Darby Bovine Kidney (MDBK), Madin-Darby Canine Kidney (MDCK) VERO (Green Monkey) Porcine Kidney (PK), CrFk (Crandel-Feline Kidney) McCoy and/or anchor-independent (suspension cultures) and the like, which can be added as HS or a form of HS, and/or co-cultivated and/or co-passaged in media or culture media for activation of the Treponemes. These cell cultures are references from American Type Culture Collection (ATCC), and are hereby incorporated by reference herein.

The addition of primary cells or primary cell cultures or CCL's, or skin explants and the like to the Treponemes is believed to be distinct from any previous reports. In the previous publications, Treponemes were added to primary cells or primary cell cultures or CCL, or skin explants and/or cell cultures and not vice-versa. In the previous publications, the reason and focus of adding Treponemes to primary cells, primary cell cultures, CCL or skin explants was to determine the cause or effect of the Treponemes on the living primary cells, primary cell cultures, CCL or skin explants and not the reverse. Nebel, U.; Mülling, Ch.; Nordhoff, M.; Budras, K. "In Vitro Infectioion (sic) of Bovine Hoof Cells and Skin Explants with *Treponema Brennaborense* and *Treponema Denticola*" Anatomia, Histologia, Embryologia, Volume 34, Issue Supplement s1, pages 37-38, December 2005. U. Nebel, Ch. K. W. Mülling, M. Nordhoff, K.-D. Budras "IN VITRO INFECTION OF BOVINE EPIDERMAL CELLS AND BOVINE SKIN EXPLANTS WITH TREPONEMES" *Proceedings of the 13th International Symposium and 5th Conference on Lameness in Ruminants*, 11-15 February (2004), Maribor, Slovenija. Stuart Carter, Nicholas Evans, Donna Timofte, Jennifer Brown, Roger Blowey, Richard Murray, Richard Birtles and Tony Hart, "DERMATITIS—MICROBIAL AETIOPATHOGENESIS APPROACHES PROVIDING OPPORTUNITIES FOR TREATMENT" *Proceedings of the Cattle Lameness Conference* Sutton Bonington, p 9-18 University of Bristol, The Dairy Group and University of Nottingham, (2009).

More specifically, in this embodiment, HS is added to or co-cultivated or grown with media containing the Treponemes to determine and focus on the HS activated Treponemes and not the HS. This is a clear distinction from the prior art.

It is believed the significance, simplicity and novelty of adding HS, and/or co-culturing and/or co-cultivating HS with Treponemes is far reaching. It is believed that when the Treponemes are grown in a media absent of HS, subcultured from the original biopsy or tissue sample, as it is currently done as a standard in the art and distinct from this instant invention, many genes involved in pathogenesis are down regulated and/or shut off. However, as illustrated in the above embodiments, HS activated Treponemes reproducibly and reliably demonstrated an expressed protein at the 38-49 kDa range. The HS induced protein expression has immunological significance as demonstrated by the immunoblots. It is believed that this protein and its corresponding gene or genes is part of the Treponemal pathogenesis of DD and gingivitis. This is evidenced by all of the naturally PDD infected animals tested thus far have demonstrated specific antibodies to the HS induced protein. It is believed, this highly conserved function of gene regulation in the Treponemes demonstrates its ability of adapting to its environment and its resultant pathogenesis whether in the skin and/or hoof skin of a cow, the coronary band in sheep or the gingival areas in humans.

It is further believed that using different forms of HS and/or different treatments of HS can result in additional gene activation and/or protein expression, within all of the Treponemes, including the Treponemes that have a greater than 98% DNA homology to *T. denticola* and those Treponemes and/or spirochetes that do not have a greater than 98% DNA homology to *T. denticola*.

It is further believed that Treponemal location in HS during its in vivo pathological state or condition is based on the Treponemes "food" supply, e.g. HS, and constituents of its "food" supply, e.g. HS. It has been demonstrated in Kiltgaard et al. "Evidence of Multiple *Treponema Phylotypes* Involved in Bovine Digital Dermatitis as Shown by 16S rRNA Gene Analysis and Fluorescence In Situ Hybridization" Journal of Clinical Microbiology, Vol. 46 No. 9 (2008), that each *Treponema phylotype* was "confined" to a specific area of the I-IS, which, in this embodiment, it is believed represents the Treponemes ability to detect its food supply, e.g. HS, and then commit to its food supply, e.g. HS.

Although the present invention has been fully described in connection with embodiments thereof with reference to the accompanying drawings, it is to be noted that various changes and modifications will become apparent to those skilled in the art. Such changes and modifications are to be understood as being included within the scope of the present invention as defined by the appended claims.

The invention has been described with reference to various specific and preferred embodiments and techniques. However, it should be understood that many variations and modifications may be made while remaining within the spirit and scope of the invention.

The Inventor acknowledges the work and participation of Hans P. Riemann, deceased and "in memory of."

The invention claimed is:

1. A vaccine for the immunization of ungulates against Treponemes, comprising:
   an effective immunogenic amount of HS activated or HS induced *Treponema* spirochetes, fragments of said HS activated or HS induced spirochetes, polypeptides of said HS activated or HS induced spirochetes, subunit proteins of said HS activated or HS induced spirochetes, recombinant of said polypeptide(s), recombinant of said subunit protein(s), vector/plasmid expressing said polypeptide(s) and vector/plasmid expressing said subunit(s) wherein all of the components are dispersed in a physiologically acceptable non-toxic liquid vehicle, and
   wherein HS is defined as mammalian Hair and Skin and/or skin, and/or skin explants that are not used as a biopsy for isolation of Treponemes; and
   wherein the immunogenic *Treponema* spirochetes are obtained according to the process comprising:
   (i) isolating skin and/or tissue and/or blood from ungulates infected with *Treponema* spirochetes; and then
   (ii) subculturing, co-cultivating, growing, culturing, and/or passaging the isolated *Treponema* spirochetes with HS.

2. The vaccine of claim 1, wherein the Treponemes are involved in Papillomatous Digital Dermatitis (PDD), Contagious Ovine Digital Dermatitis (CODD), Digital Dermatitis (DD) and/or ungulate gingivitis.

3. A method for the immunization of an ungulate against PDD and CODD and/or ungulate gingivitis comprising administration of an effective amount of the vaccine of claim 1 to said ungulate.

4. The method of claim 3, wherein the vaccine is administered by injection.

5. The method of claim 4, wherein a plurality of injections of the vaccine are administered.

6. The method of claim 3, wherein the vaccine is combined with at least one of leptospiral bacteria and/or bovine, ovine and/or ungulate vaccines.

7. The vaccine of claim 1, further comprising an effective amount of adjuvant.

* * * * *